United States Patent
Goletz et al.

(10) Patent No.: US 10,184,135 B2
(45) Date of Patent: Jan. 22, 2019

(54) EUKARYOTIC EXPRESSION VECTORS COMPRISING REGULATORY ELEMENTS OF THE GLOBIN GENE CLUSTERS

(71) Applicant: Glycotope GmbH, Berlin (DE)

(72) Inventors: Steffen Goletz, Berlin (DE); Doreen Jahn, Berlin (DE); Antje Danielczyk, Berlin (DE)

(73) Assignee: Glycotope GmbH, Berlin (DE)

( * ) Notice: Subject to any disclaimer, the term of this patent is extended or adjusted under 35 U.S.C. 154(b) by 0 days.

(21) Appl. No.: 15/559,272

(22) PCT Filed: Mar. 30, 2016

(86) PCT No.: PCT/EP2016/056926
§ 371 (c)(1),
(2) Date: Sep. 18, 2017

(87) PCT Pub. No.: WO2016/156404
PCT Pub. Date: Oct. 6, 2016

(65) Prior Publication Data
US 2018/0094279 A1    Apr. 5, 2018

(30) Foreign Application Priority Data
Mar. 31, 2015  (EP) ..................... 15161922
Mar. 31, 2015  (LU) .......................... 92686

(51) Int. Cl.
| | |
|---|---|
| *C12P 21/02* | (2006.01) |
| *C12N 15/85* | (2006.01) |
| *C07K 14/47* | (2006.01) |
| *C12N 15/66* | (2006.01) |
| *G01N 33/50* | (2006.01) |
| *C07K 14/59* | (2006.01) |
| *C07K 14/715* | (2006.01) |

(52) U.S. Cl.
CPC ............ *C12N 15/85* (2013.01); *C07K 14/473* (2013.01); *C12N 15/66* (2013.01); *G01N 33/5047* (2013.01); *C07K 14/59* (2013.01); *C07K 14/7151* (2013.01)

(58) Field of Classification Search
None
See application file for complete search history.

(56) References Cited

U.S. PATENT DOCUMENTS

| | | |
|---|---|---|
| 6,524,851 B1 | 2/2003 | Ellis |
| 2004/0133934 A1 | 7/2004 | Townes et al. |

OTHER PUBLICATIONS

Calzolari, R. et al., "Deletion of a region that is a candidate for the difference between the deletion forms of hereditary persistence of fetal hemoglobin and [delta] [beta]-thalassemia affects [beta]-but not [gamma]-globin gene expression," The EMBO Journal, vol. 18(4): 949-958 (1999) XP055202892.

International Search Report and Written Opinion, PCT/EP2016/056926, dated Jun. 13, 2016, 12 pages.

Lung, H. et al., "In vivo silencing of the human gamma-globin gene in murine erythroid cells following retroviral transduction," Blood Cells Mol Dis., vol. 26(6):613-619 (2000).

Migliaccio, G. et al., "Spontaneous switch from A-gamma-to beta-globin promoter activity in a stable transfected dual reporter vector," Blood Cells, Molecules and Diseases, vol. 34(2):174-180 (2005).

*Primary Examiner* — James S Ketter
(74) *Attorney, Agent, or Firm* — Nelson Mullins Riley & Scarborough LLP; Jane E. Remillard, Esq.; Jill Gorny Sloper, Esq.

(57) ABSTRACT

The present invention pertains to the field of recombinant protein production. Novel expression cassettes comprising elements of the human globin gene clusters are provided which show enhanced expression rates of proteins or polypeptides of interest.

Figure 1:
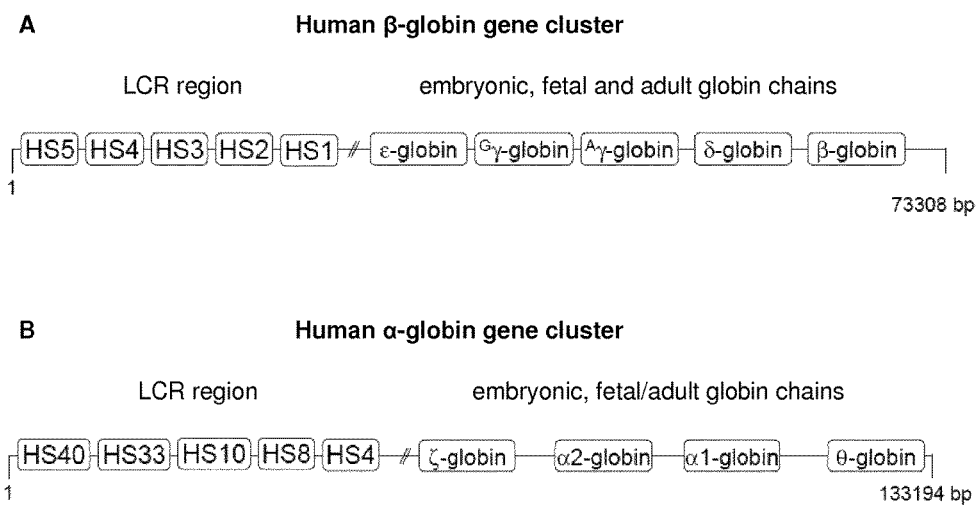

23 Claims, 5 Drawing Sheets
Specification includes a Sequence Listing.

EUKARYOTIC EXPRESSION VECTORS COMPRISING REGULATORY ELEMENTS OF THE GLOBIN GENE CLUSTERS

CROSS REFERENCE TO RELATED APPLICATIONS

This application is a 35 U.S.C. 371 national stage filing of International Application No. PCT/EP2016/056926, filed on Mar. 30, 2016, which claims priority from Luxembourg Patent Application No. 92686, filed Mar. 31, 2015 and European Patent Application No. 15161922.8, filed Mar. 31, 2015. The contents of the aforementioned applications are hereby incorporated by reference in their entireties.

SEQUENCE LISTING

The instant application contains a Sequence Listing which has been submitted electronically in ASCII format and is hereby incorporated by reference in its entirety. Said ASCII copy, created on Sep. 18, 2017, is named KNJ_043US_SL.txt and is 16,942 bytes in size.

FIELD OF THE INVENTION

The present invention pertains to novel expression cassettes which can be used to enhance the production yield of a protein of interest. The expression cassettes comprise expression regulation elements of the human globin gene clusters, in particular the promoter of the human $^A\gamma$ globin and the locus control region of the human β-globin or α-globin gene cluster. The present invention in particular provides an expression cassette comprising such globin expression regulation elements.

BACKGROUND OF THE INVENTION

Recombinant protein production is a major aspect of the biotechnical industry of today. It is gaining more and more importance as the number of applications requiring high amounts of high-quality proteins increase on the market. Food production and in particular pharmacology are two main areas where the need for recombinant proteins steadily increases. Higher production efficiencies and consequently lower costs of the final product are needed for obtaining a commercially viable process.

However, at the same time a high product quality and compatibility with human applications is essential. More and more applications required recombinant production of the proteins in eukaryotic cells, in particular in higher eukaryotic cells. Especially proteins carrying post-translational modifications such a glycosylation (glycoproteins) significantly differ when expressing them in prokaryotic cell systems such as *E. coli* or eukaryotic cell systems such as in particular human cell lines. These differences in many cases markedly affect the biological activity as well as the immunogenicity of the produced proteins. However, many expression systems using higher eukaryotic cell lines suffer from a rather low expression rate of the desired protein, resulting in low yields and high costs of the recombinant protein.

Therefore, there is a need in the art to provide novel means and methods for increasing the yield of recombinant protein production, especially when using eukaryotic expression cell lines.

SUMMARY OF THE INVENTION

As demonstrated by the present invention, certain elements of the human globin gene clusters can be combined to provide an expression cassette which enables stable and high expression of polypeptides of interest in eukaryotic cells. In particular, the combination of specific parts of the locus control region of the β-globin gene cluster or the α-globin gene cluster with the $^A\gamma$ globin promoter and optionally also the $^A\gamma$ globin 3' enhancer forms an expression cassette with surprisingly high and stable expression rates.

Therefore, the present invention provides in a first aspect a method for recombinantly producing a polypeptide of interest, comprising the steps of
(a) providing a host cell which comprises an expression cassette comprising, functionally linked to each other,
  (i) a locus control region comprising at least a functional part of the locus control region of the human β-globin gene cluster or the human α-globin gene cluster;
  (ii) a promoter region comprising at least a functional part of the promoter of the human $^A\gamma$ globin gene; and
  (iii) a coding region comprising a nucleic acid sequence encoding the polypeptide of interest;
(b) culturing the host cell under conditions at which the host cell expresses the polypeptide of interest; and
(c) isolating the polypeptide of interest.

In a second aspect, the present invention provides an expression cassette comprising, functionally linked to each other,
(i) a locus control region comprising at least a functional part of the locus control region of the human β-globin gene cluster or the human α-globin gene cluster;
(ii) a promoter region comprising at least a functional part of the promoter of the human $^A\gamma$ globin gene;
(iii) optionally a coding region;
(iv) a transcription terminator region; and
(v) an enhancer region comprising at least a functional part of the 3' enhancer of the human $^A\gamma$ globin gene;
wherein the expression cassette does not comprise a nucleic acid sequence coding for the entire human $^A\gamma$ globin.

In a third aspects, the present invention provides a vector comprising the expression cassette according to the second aspect and a host cell comprising said expression cassette or said vector.

Other objects, features, advantages and aspects of the present invention will become apparent to those skilled in the art from the following description and appended claims. It should be understood, however, that the following description, appended claims, and specific examples, which indicate preferred embodiments of the application, are given by way of illustration only. Various changes and modifications within the spirit and scope of the disclosed invention will become readily apparent to those skilled in the art from reading the following.

Definitions

As used herein, the following expressions are generally intended to preferably have the meanings as set forth below, except to the extent that the context in which they are used indicates otherwise.

The expression "comprise", as used herein, besides its literal meaning also includes and specifically refers to the expressions "consist essentially of" and "consist of". Thus, the expression "comprise" refers to embodiments wherein the subject-matter which "comprises" specifically listed elements does not comprise further elements as well as embodiments wherein the subject-matter which "comprises" specifically listed elements may and/or indeed does encompass further elements. Likewise, the expression "have" is to be understood as the expression "comprise", also including and specifically referring to the expressions "consist essentially of" and "consist of".

The term "nucleic acid" as used herein refers to a ribonucleotide or desoxyribonucleotide polymer. A nucleic acid may be RNA or DNA. It may be composed of a single polymer strand or it may be double-stranded. The nucleic acid may be of natural, recombinant or synthetic origin. In preferred embodiments, a nucleic acid is a double-stranded DNA.

An "expression cassette" is a nucleic acid construct, generated or synthesized, with nucleic acid elements that are capable of effecting expression of a structural gene in hosts that are compatible with such sequences. Expression cassettes include at least a promoter and optionally, transcription termination signals. Typically, the expression cassette includes a nucleic acid to be transcribed and a promoter. Additional factors helpful in effecting expression may also be used as described herein. For example, an expression cassette can also include nucleotide sequences that encode a signal sequence that directs secretion of an expressed protein from the host cell. An expression cassette preferably is part of an expression vector. Host cells which shall be used for expression of the nucleic acid to be transcribed are transformed or transfected with the expression vector. To allow selection of transformed cells comprising the constructs, a selectable marker gene can be conveniently included in the expression vectors. A person having skill in the art will recognize that this vector component can be modified without substantially affecting its function.

The expression "functionally linked" means that two or more elements of an expression cassette are linked to one another in such a way that their function is coordinated and allows expression of the coding sequence (e.g. the coding region). By way of example, a promoter is functionally linked to a coding sequence when it is capable of ensuring expression of said coding sequence. The construction of an expression cassette according to the invention and the assembly of its various elements can be carried out using techniques well known to those skilled in the art, in particular those described in Sambrook et al. (1989, Molecular Cloning: A Laboratory Manual, Nolan C. ed., New York: Cold Spring Harbor Laboratory Press).

The terms "upstream" and "downstream" as used herein refer to the position of a nucleic acid element or sequence on a nucleic acid molecule with respect to another nucleic acid element or sequence on said nucleic acid molecule. "Upstream" refers to a position which is nearer to the 5' end of the nucleic acid molecule and "downstream" refers to a position which is nearer to the 3' end of the nucleic acid molecule. In case of double-stranded nucleic acids, in particular DNA, that strand of the nucleic acid which is used as matrix for transcription of an RNA such as an mRNA, i.e. the sense strand, is used to determine the 5' end and the 3' end of the nucleic acid. Hence, "upstream" is in the direction of the 5' end of the sense strand while "downstream" is in the direction of the 3' end of the sense strand.

A "homologue" of a target nucleic acid sequence or amino acid sequence shares a homology or identity of at least 75%, more preferably at least 80%, at least 85%, at least 90%, at least 93%, at least 95%, at least 96%, at least 97%, at least 98% or at least 99% with said target nucleic acid sequence or amino acid sequence. A "homology" or "identity" of an amino acid sequence or nucleotide sequence is preferably determined according to the invention over the entire length of the target sequence or over the entire length of the indicated part of the target sequence. When referring to a specific nucleic acid sequence or amino acid sequence, the present invention generally also encompasses homologues of said nucleic acid sequence or amino acid sequence, respectively. A homologue of a target nucleic acid sequence or amino acid sequence in particular is a functional homologue which has the same or substantially the same functions and activities of the target nucleic acid sequence or amino acid sequence from which it is derived.

A "promoter" is a nucleic acid sequence which allows and controls transcription of a nucleic acid sequence functionally linked thereto, in particular a coding sequence. A promoter contains a recognition sequence for binding RNA polymerase and includes or is functionally linked to a transcription initiation site. The promoter may be an inducible promoter which is only active in the presence (or absence) of a specific signal, or it may be constitutively active. The activity of the promoter may be further regulated by regulatory elements such as locus control regions and enhancer elements.

A "coding sequence" is a nucleic acid sequence encoding a gene product such as a polypeptide or RNA.

A "part" of a nucleic acid element in particular comprises at least 5 nucleic acids, preferably at least 10, at least 15, at least 20, at least 30 or at least 50 nucleic acids of said nucleic acid element. A "part" of a nucleic acid element in particular comprises at least 5 consecutive nucleotides, preferably at least 10, at least 15, at least 20, at least 30 or at least 50 consecutive nucleotides of said nucleic acid element. In particular, it comprises at least 1%, preferably at least 2%, at least 3%, at least 5%, at least 7.5%, at least 10%, at least 15%, at least 20% or at least 25% of said nucleic acid element. A "functional part" of a nucleic acid element is a part of said element which is capable of performing the intended function of the element. For example, a functional part of a locus control region, promoter or 3' enhancer is capable of modulating, in particular enhancing the expression of a coding region to which it is functionally linked. A part of a nucleic acid element in particular refers to a functional part of said nucleic acid element.

A "peptide" or "polypeptide" as used herein refers to a polypeptide chain comprising at least 5 amino acids. A peptide or polypeptide preferably comprises at least 10, at least 15, at least 20, at least 25, at least 30 or at least 35 amino acids. The term "peptide" or "polypeptide" as used herein also refers to proteins, including peptides, polypeptides and proteins which were post-translationally modified. In particular, the term peptide or polypeptide includes glycosylated peptides and glycoproteins. The terms "peptide" and "polypeptide" are used interchangeably herein.

A part of a peptide, polypeptide or protein preferably comprises at least 3 consecutive amino acids of said peptide, polypeptide or protein, preferably at least 5, at least 10, at least 15 or at least 20 consecutive amino acids of said protein.

The term "pharmaceutical composition" and similar terms particularly refers to a composition suitable for administering to a human, i.e., a composition containing components which are pharmaceutically acceptable. Preferably, a pharmaceutical composition comprises an active compound or a salt or prodrug thereof together with a carrier, diluent or pharmaceutical excipient such as buffer, preservative and tonicity modifier.

DETAILED DESCRIPTION OF THE INVENTION

The present invention is directed to an expression cassette comprising at least part of a locus control region of a human globin gene cluster and a human $^A\gamma$ globin promoter.

Hemoglobin is a metalloprotein in the blood of humans and animals which enables the transport of oxygen and carbon dioxide. Hemoglobin is a multi-subunit globular protein comprised of four subunits (globins), each consisting of a polypeptide chain closely associated with a heme group which carries an iron ion. There are several different types of globin subunits and the subunit composition of hemoglobin changes throughout life. For example, the human fetus has hemoglobin F composed of two globin α and two globin γ ($α_2γ_2$), while in the adult hemoglobin A with two globin α and two globin β ($α_2β_2$) predominates. The different globin polypeptides are expressed by the human globin gene clusters which are responsible for expression of the different subunits in the different developmental states of the human being. The human β-globin gene cluster comprises a locus control region and five different globin genes, i.e. the ε-, $^Gγ$-, $^Aγ$-, δ- and β-globin gene. Likewise, the α-globin gene cluster also comprises a locus control region and the ζ-, α2-, α1- and θ-globin genes. FIG. 1 shows the structure of the human α- and β-globin gene clusters. Each separate globin gene within the gene cluster has its own specific promoter and enhancer sequences which control the expression of the coding sequence of the respective globin subunit. However, these promoters are themselves regulated by the locus control region. In particular, the locus control region is capable of activating or inactivating the promoters and this activation pattern changes throughout the lifetime. Both locus control regions (one in the α-globin gene cluster and one in the β-globin gene cluster) hence orchestrate the expression of the different globin genes during development, resulting in the specific subunit composition of the different hemoglobin proteins.

The locus control regions comprise several DNase I hypersensitivity sites (HS) which are responsible for activation and inactivation of the promoters. It has been found that, for example, HS2 of the β-globin gene cluster controls the activity of the $^Aγ$ globin promoter. HS2 of the β-globin gene cluster can be further subdivided into a core region and modulatory subdomains. The core region is that part of HS2 which is mainly responsible for activation of the globin promoter. The modulatory subdomains M1 to M5 modulate the effect of the core domain, either positively or negatively. The core region is positioned between modulatory subdomains M1 and M2, with M3 to M5 following thereafter. In particular M1 and M2 further enhance the activating effect of the core region on the $^Aγ$ globin promoter.

It was now found that the use of expression elements of the human globin gene clusters provide for a stable and high expression of a target product such as a polypeptide of interest in eukaryotic cells, in particular in human blood cells or cells derived therefrom. The present invention provides an expression cassette comprising at least a functional part of the human $^Aγ$ globin promoter and at least a functional part of a locus control region of the human α-globin or β-globin gene cluster. The expression cassette further comprises a coding region which contains a nucleic acid sequence encoding a polypeptide of interest and/or a cloning site for introduction of such a coding region. The expression cassette may further comprise an enhancer region comprising at least a functional part of a 3' enhancer of the human $^Aγ$ globin gene. The locus control region, promoter and 3' enhancer are all positioned in the expression cassette so that they can modulate and in particular enable and enhance the expression of the coding region. The expression cassette also may comprise a transcription terminator region where transcription of the coding region is terminated. The elements of the expression cassette in particular are functionally linked to each other.

Figure 2:
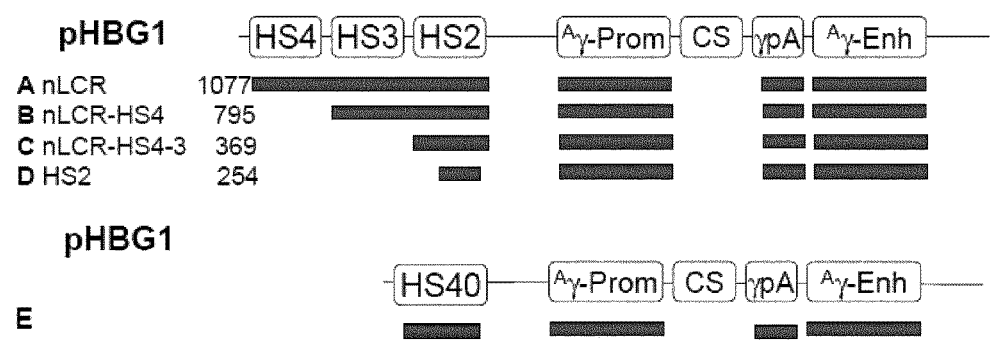

Specific examples of the expression cassette comprise or consist of the nucleic acid sequence of any one of SEQ ID NOs: 1 to 5. Respective expression elements are also shown in FIG. 2 wherein the different elements of the expression cassettes are indicated. In particular, HS4, HS3, HS2, and HS40 are parts of the locus control region of the human α-globin or β-globin gene cluster. Following this locus control region, the functional part of the human $^Aγ$ globin promoter ($^Aγ$-Prom) is indicated. Thereafter, a coding sequence or cloning site for introduction of a coding sequence (CS) and a transcription terminator region including a polyadenylation signal (γpA) follow. At the end of the expression cassette, the functional part of a 3' enhancer of the human $^Aγ$ globin gene ($^Aγ$-Enh) is positioned.

In certain embodiments, the expression cassette does not comprise a β-globin intron 2, in particular any intron of a β-globin gene or any other globin gene.

The Human $^Aγ$ Globin Promoter

The expression cassette uses a functional part of the human $^Aγ$ globin promoter for enabling and controlling expression of the coding region, in particular the polypeptide of interest. The functional part of the human $^Aγ$ globin promoter is in particular positioned upstream of the coding region. It is functionally linked to the coding region and allows and controls transcription thereof. In certain embodiments, the functional part of the human $^Aγ$ globin promoter encompasses a transcription initiation site where transcription of the premature mRNA starts. Furthermore, the functional part of the human $^Aγ$ globin promoter may also comprise at least part of a 5' untranslated region (5' UTR), in particular at least part of the 5' UTR of the human $^Aγ$ globin gene. In specific embodiments, the functional part of the human $^Aγ$ globin promoter encompasses at least that part of the human $^Aγ$ globin gene which allows transcription of the human $^Aγ$ globin mRNA. In certain embodiments, the functional part of the human $^Aγ$ globin promoter comprises a CCAAT box. In particular, the functional part of the human $^Aγ$ globin promoter comprises or consists of nucleotides −299 to −26, especially nucleotides −299 to +36, nucleotides −384 to −26, or nucleotides −384 to +36, with respect to the transcription initiation site, of the human $^Aγ$ globin gene. In particular, the functional part of the human $^Aγ$ globin promoter comprises and especially consists of the nucleic acid sequence of position 1123 to 1542 of SEQ ID NO: 1. It is also possible to use shorter fragments of the human $^Aγ$ globin promoter which are still functional. The person skilled in the art is capable of determining suitable functional parts of the human $^Aγ$ globin promoter. In particular, methods for determining the activity of a promoter sequence are known in the art and described in the examples, below.

Alternatively, a homologue of said functional part of the human $^Aγ$ globin promoter may be used according to the present invention. Said homologue preferably is at least 85%, preferably at least 90%, at least 95%, at least 97%, at least 98% or at least 99% identical with one of the nucleic acid sequences defined above over its entire length. In certain embodiments, the homologue has the same or substantially the same function and/or activity as the functional part of the $^Aγ$ globin promoter from which it is derived, and in particular provides an expression rate of the coding region which reaches at least 75%, preferably at least 80%, at least 85% or at least 90% of the expression rate reached by using the functional part of the $^Aγ$ globin promoter from which it is derived under the same conditions.

The Locus Control Region

The locus control region is functionally linked to the promoter region and is capable to modulate and in particular enhance the activity of the functional part of the human $^A\gamma$ globin promoter. The locus control region in particular is positioned upstream of the promoter region.

In certain preferred embodiments, the locus control region or a functional part thereof of the human β-globin gene cluster is used. According to the art, the human β-globin locus control region encompasses four erythroid specific DNase I hypersensitivity sites termed HS1 to HS4 located 6 to 20 kbp upstream of the first globin gene of this gene cluster, i.e. the ε-globin gene. In particular HS2 is responsible for controlling expression of the globin genes and is considered to constitute a major functional component of the locus control region. HS2 of the human β-globin locus control region is subdivided into a core element and further modulatory subdomains, wherein the core element is positioned between the modulatory subdomains M1 and M2. The core element is the minimal region of the β-globin locus control region which is capable of enhancing the promoter activity of the human $^A\gamma$ globin promoter.

In a preferred embodiment, the locus control region comprises the core element of the DNAse I hypersensitivity site 2 (HS2) of the human β-globin gene cluster. In particular, the core element of HS2 of the human β-globin gene cluster has the nucleic acid sequence of position 906 to 939 of SEQ ID NO: 1. In certain embodiments, the locus control region comprises or consists of the core element of HS2 and the two adjacent modulatory subdomains M1 and M2, i.e. the M1-core-M2 element of HS2 of the human β-globin gene cluster. Said M1-core-M2 element may have the nucleic acid sequence of position 742 to 995 of SEQ ID NO: 1. It hence includes the core region of HS2 having the nucleic acid sequence of position 906 to 939 of SEQ ID NO: 1.

In a further embodiment, the locus control region comprises at least a functional part of the hypersensitivity site 2 (HS2) of the human β-globin gene cluster which comprises the nucleic acid sequence of position 741 to 1109 of SEQ ID NO: 1. This functional part of HS2 comprises the M1-core-M2 element and an additional nucleic acid sequence directly downstream thereof.

In certain embodiments, the locus control region which comprises at least a functional part of HS2 of the human β-globin gene cluster further comprises at least a part of the hypersensitivity site 3 (HS3) of the human β-globin gene cluster. In particular, the HS3 or part thereof is positioned upstream of the HS2 or part thereof in the locus control region of the expression cassette. The HS3 or part thereof in particular comprises or consists of the nucleic acid sequence of position 310 to 735 of SEQ ID NO: 1. Furthermore, the locus control region may also comprise the hypersensitivity site 4 (HS4) or a part thereof of the human β-globin gene cluster, which in particular is positioned upstream of HS2 and HS3, if present. In certain embodiments, HS4 or the part thereof comprises or consists of the nucleic acid sequence of position 13 to 294 of SEQ ID NO: 1. Hence, the locus control region of the expression cassette according to the invention may comprise, in downstream direction, optionally at least a part of HS4, optionally at least a part of HS3, and at least a functional part of HS2 of the human β-globin gene cluster. In alternative embodiments, the locus control region does not comprise the hypersensitivity site 3 (HS3) of the human β-globin gene cluster.

In particular embodiments, the locus control region has a nucleic acid sequence selected from the group consisting of position 13 to 1109 of SEQ ID NO: 1, position 20 to 819 of SEQ ID NO: 2, position 18 to 386 of SEQ ID NO: 3 and position 13 to 266 of SEQ ID NO: 4.

In another embodiment, the locus control region comprises at least a functional part of the hypersensitivity site 40 (HS40) of the human α-globin gene cluster. The part of HS40 in particular comprises or consists of the core element of HS40 which may have the nucleic acid sequence of position 24 to 278 of SEQ ID NO: 5. In particular, HS40 or the part thereof comprises or consists of the nucleic acid sequence of position 7 to 372 of SEQ ID NO: 5.

Furthermore, in certain embodiments a locus control region can be used comprising or consisting of a nucleic acid sequence which is a homologue of one of the above locus control regions. In particular, said homologue has a sequence identity of at least 90%, preferably at least 95%, at least 97%, at least 98% or at least 99% with one of the above locus control regions over the entire length, and/or has the same or substantially the same function as the locus control region from which it is derived. In preferred embodiments, the homologue locus control region provides an expression rate of the coding region which reaches at least 75%, preferably at least 80%, at least 85% or at least 90% of the expression rate reached by using the locus control region from which it is derived under the same conditions.

The Coding Region

The coding region of the expression cassette comprises a nucleic acid sequences coding for a product of interest, in particular a polypeptide of interest, which is to be expressed by the expression cassette. The expression of the nucleic acid sequences of the coding region is regulated by the promoter region and hence, is functionally linked thereto. When the expression cassette, optionally present in a vector, is introduced into a suitable host cell, said host cell produces a product, in particular a polypeptide, encoded by the nucleic acid sequences of the coding region.

The coding region of the expression cassette in particular contains or consists of a nucleic acid sequence coding for a polypeptide of interest.

The polypeptide of interest may be any polypeptide, including proteins. The polypeptide may be of any origin, including mammalian- and human-derived polypeptides as well as artificial polypeptides. In certain embodiments, the polypeptide comprises one or more glycosylation sites and in particular is a glycosylated polypeptide such as a glycoprotein or a part thereof. Antibodies or derivatives or parts thereof; peptide hormones, gonadotropins such as FSH (follicle-stimulating hormone), CG (chorionic gonadotropin), LH (luteinizing hormone) and TSH (thyroid-stimulating hormone) including all isoforms and variants thereof; erythropoietin; blood clotting factors such as factor VII, VIII, IX or von Willebrand factor; lysosomal enzymes and cytokines. Furthermore, the polypeptide of interest may be selected from the group consisting of any of the protein molecule of the group of cytokines and their receptors, for instance the tumor necrosis factors TNF-alpha and TNF-beta; renin; human growth hormone and bovine growth hormone; growth hormone releasing factor; parathyroid hormone; thyroid stimulating hormone; lipoproteins; alpha-1-antitrypsin; insulin A-chain and B-chain; gonadotrophins, e.g. follicle stimulating hormone (FSH), luteinizing hormone (LH), thyrotrophin, and human chorionic gonadotrophin (hCG); calcitonin; glucagon; clotting factors such as factor VIIIC, factor IX, factor VII, tissue factor and von Willebrands factor; anti-clotting factors such as protein C; atrial natriuretic factor; lung surfactant; plasminogen activators, such as urokinase, human urine and tissue-type plasminogen activator; bombesin; thrombin; hemopoietic growth factor; enkephalinase; human macrophage inflammatory protein; a serum albumin such as human serum albumin; mullerian-inhibiting substance; relaxin A-chain and B-chain; prorelaxin; mouse gonadotropin-associated peptide; vascular endothelial growth factor; receptors for hormones or growth factors; integrin; protein A and D; rheumatoid factors; neurotrophic factors such as bone-derived neurotrophic factor, neurotrophin-3, -4, -5, -6 and nerve growth factor-beta; platelet-derived growth factor; fibroblast growth factors; epidermal growth factor; transforming growth factor such as TGF-alpha and TGF-beta; insulin-like growth factor-I and -II; insulin-like growth factor binding proteins; CD proteins such as CD-3, CD-4, CD-8 and CD-19; erythropoietin (EPO); osteoinductive factors; immunotoxins; a bone morphogenetic protein; an interferon such as interferon-alpha, -beta, and -gamma; colony stimulating factors (CSF's), e.g. M-CSF, GM-CSF and G-CSF; interleukins (IL's), e.g. IL-1 to IL-12; superoxide dismutase; T-cell receptors; surface membrane proteins; decay accelerating factor; antibodies and immunoadhesins; glycophorin A; and mucin proteins such as MUC1.

In certain embodiments, the polypeptide of interest is an antibody or a part or derivative thereof. In particular, the polypeptide of interest may be the heavy chain or the light chain of an antibody or a part thereof. Furthermore, the polypeptide of interest may be a part or derivative of an antibody selected from the group consisting of (i) Fab fragments, monovalent fragments consisting of the variable region and the first constant domain of each the heavy and the light chain; (ii) F(ab)$_2$ fragments, bivalent fragments comprising two Fab fragments linked by a disulfide bridge at the hinge region; (iii) Fd fragments consisting of the variable region and the first constant domain CH1 of the heavy chain; (iv) Fv fragments consisting of the heavy chain and light chain variable region of a single arm of an antibody; (v) scFv fragments, Fv fragments consisting of a single polypeptide chain; (vi) (Fv)$_2$ fragments consisting of two Fv fragments covalently linked together; (vii) a heavy chain variable domain; and (viii) multibodies consisting of a heavy chain variable region and a light chain variable region covalently linked together in such a manner that association of the heavy chain and light chain variable regions can only occur intermolecular but not intramolecular. In embodiments wherein the expression cassette includes a coding region coding for an antibody or a part or derivative thereof, the locus control region in particular comprises at least a part of HS2 of the human β-globin gene cluster, preferably at least a part of HS2 and at least a part of HS3 of the human β-globin gene cluster or at least a part of HS2 and at least a part of HS4 of the human β-globin gene cluster, especially at least a part of HS2 and at least a part of HS3 and at least a part of HS4 of the human β-globin gene cluster.

In certain embodiments, the coding region encodes more than one polypeptide, in particular two polypeptides. In these embodiments, the coding region may contain two or more separate nucleic acid sequences which transcribe into separate mRNAs, each having its own transcription initiation site, transcription termination site and polyadenylation signal. Alternatively, the coding region may contain a nucleic acid sequence which transcribe into an mRNA which comprises two or more separate coding nucleic acid sequences which each encode a separate polypeptide. In these embodiments, the coding region may comprise one or more internal ribosomal entry sites, one for each coding nucleic acid sequence in addition to the first one. These internal ribosomal entry sites allow the translation of more than one polypeptide from a single transcript. In certain embodiments, the coding region encodes two polypeptides, in particular the heavy chain and the light chain of an antibody.

In certain embodiments, the coding region comprises a nucleic acid sequence coding for a signal peptide which in particular comprises an extracellular localization signal. The nucleic acid sequence coding for a signal peptide may be the only coding sequence of the coding region or may be present in addition to further coding sequences, such as those nucleic acid sequences coding for a polypeptide as described above. The signal peptide in particular induces a secretory expression of the polypeptide of interest encoded by the coding region. The signal peptide may be cleaved off from the remaining polypeptide during the expression. The signal peptide in particular is positioned upstream of the other coding nucleic acid sequences comprised in the coding region or upstream of the cloning site, in particular at the beginning of the coding region. Furthermore, the nucleic acid sequence coding for the signal peptide is positioned in frame with the other coding nucleic acid sequences comprised in the coding region.

In particular embodiments, the coding region comprises the nucleic acid sequence coding for a polypeptide of interest.

In certain embodiments, the coding region does not comprise a reporter gene or a selectable marker gene. In further embodiments, the coding region does not comprise a nucleic acid sequence coding for a globin protein or a part thereof comprising at least 20 consecutive amino acids of a globin protein.

The Cloning Site

In certain embodiments, the expression cassette comprises a cloning site for integrating a nucleic acid sequence. The cloning site may be present in the expression cassette instead of the coding region and may serve for introducing said nucleic acid sequence into the expression cassette. Furthermore, the cloning site may be present in the expression cassette in addition to the coding region, in particular in embodiments wherein the coding region only comprises a nucleic acid sequence coding for a signal peptide.

The cloning site present in the expression cassette is suitable for introducing a coding region, in particular a nucleic acid coding for a polypeptide of interest, into the expression cassette. Suitable cloning sites and methods for introducing nucleic acid fragments into other nucleic acid molecules such as expression cassettes or vectors are commonly known in the art. In certain embodiments, the cloning site comprises at least one, in particular at least two, at least three, at least four or at least five recognition sequences of restriction enzymes. Suitable restriction enzymes and their recognition sequences are known in the art. Exemplary restriction enzymes are EcoRI, EcoRV, HindIII, BamHI, XbaI, PvuI, KpnI, BstXI, XmaI, SmaI, NotI, XhoI and ClaI. An exemplary nucleic acid sequence of a multiple cloning site is represented by the nucleic acid sequence of position 1559 to 1664 of SEQ ID NO: 1.

The Transcription Terminator Region

In certain embodiments, the expression cassette comprises a transcription terminator region. The transcription terminator region is functionally linked with the promoter region and terminates the transcription of the coding region. It is positioned downstream of the coding region and/or cloning site.

In specific embodiments, the transcription terminator region comprises a transcription termination site and/or a polyadenylation signal. The polyadenylation signal may be any polyadenylation signal which is capable of inducing polyadenylation of the premature mRNA in eukaryotic cells, in particular in human cells. It may comprise or consist of the nucleic acid sequence of position 1725 to 1730 of SEQ ID NO: 1 or a homologue thereof.

The Enhancer Region

In certain embodiments, the expression cassette comprises an enhancer region, in particular a 3' enhancer region. The 3' enhancer region is positioned downstream of the coding region and/or cloning site and downstream of the transcription terminator region, if present. It is functionally linked with the promoter region and enhances expression of the coding region. The enhancer region in particular comprises or consists of at least a functional part of the 3' enhancer of the human $^A\gamma$ globin gene. In certain embodiments, the enhancer region comprises or consists of the nucleic acid sequence of position 2136 to 2881 of SEQ ID NO: 1 or a homologue thereof. In certain embodiments, the homologue enhancer region provides an expression rate of the coding region which reaches at least 75%, preferably at least 80%, at least 85% or at least 90% of the expression rate reached by using the enhancer region from which it is derived under the same conditions.

The Vector Comprising the Expression Cassette

In one aspect, the present invention pertains to a vector comprising the expression cassette according to the invention. The vector may be any vector suitable for transferring the expression cassette into a host cell. Respective vectors are known in the art. In particular, the vector is adapted for transfer into eukaryotic cells, such as mammalian cells, in particular human cells.

In addition to the expression cassette, the vector may comprise further elements. For example, the vector may comprise one or more selection markers. In certain embodiments, at least one of the selection markers is suitable for selecting host cells comprising the vector, in particular eukaryotic host cells, such as mammalian host cells, in particular human host cells, against host cells not comprising the vector. Suitable examples of the selection markers are genes which provide resistance against an antibiotic compound. Furthermore, the vector may comprise elements suitable for amplifying it in a prokaryotic host cell such as E. coli cells. Such elements for example include an origin of replication such as Col E1 Ori and a prokaryotic selection marker such as a gene providing resistance against a bactericide, e.g. ampicillin.

In certain embodiments, the vector is a circular or linear double-stranded DNA, in particular a circular double-stranded DNA.

In certain embodiments, the vector comprises the expression cassette with the coding region comprising a nucleic acid sequence coding for a polypeptide of interest.

The Selectable Marker Gene

In certain embodiments, the vector further comprises a selectable marker gene. The selectable marker gene does not need to be functionally linked with the elements of the expression cassette. The selectable marker gene allows for selection of host cells which comprise the vector. Cells containing the vector preferably are cultivated in the presence of a suitable selection agent which reduces or inhibits proliferation of cells not comprising the selectable marker gene.

In specific embodiments, the selectable marker gene is an amplifiable selectable marker gene which allows amplification of the marker gene and co-amplification of the expression cassette which is present on the same vector. When using an amplifiable selectable marker gene, amplification of the expression cassette in transfected cells in particular is achieved by stepwise cultivation of the cells in the presence of increasing concentrations of the selection agent. In certain embodiments, the selectable marker gene encodes a dihydrofolate reductase (DHFR), such as an antifolate resistant DHFR variant, and the corresponding selection agent is an antifolate, such as methotrexate.

Further examples of suitable amplifiable selectable marker genes and their corresponding selection agents are neomycin resistance gene (e.g. aminoglycoside phosphotransferase) and geneticin (G418); puromycin N-acetyltransferase and puromycin; metallothionein and cadmium; CAD (carbamoyl-phosphate synthetase:aspartate transcarbamylase:dihydroorotase) and N-phosphoacetyl-L-aspartate; adenosine-deaminase and Xyl-A- or adenosine, 2'deoxycoformycin; AMP (adenylate)-deaminase and adenine, azaserin, coformycin; UMP-synthase and 6-azauridine, pyrazofuran; IMP 5'-dehydrogenase and mycophenolic acid; xanthine-guanin-phosphoribosyl transferase and mycophenolic acid with limiting xanthine; mutant HGPRTase or mutant thymidine kinase and hypoxanthine, aminopterine and thymidine (HAT); thymidylate synthetase and 5-fluorodeoxyuridine; P-glycoprotein 170 (MDR1) and adriamycin, vincristin, colchicine; ribonucleotide reductase and aphidicoline; glutamine synthetase and methionine sulphoximine (MSX); asparagine synthetase and β-aspartylhydroxamate, albizziin, 5'azacytidine; argininosuccinate synthetase and canavanin; ornithine decarboxylase and α-difluoromethyl-ornithine; HMG-CoA-reductase and compactin; N-acetylglucosaminyl transferase and tunicamycin; threonyl-tRNA synthetase and borrelidin; and $Na^+K^+$-ATPase and ouabain.

The Host Cell Comprising the Expression Cassette or the Vector

In a further aspect, the present invention provides a host cell comprising the expression cassette according to the invention or the vector according to the invention. The host cell may be any cell suitable for transfection with the expression cassette or vector and in particular suitable for production of the polypeptide of interest. In certain embodiments, the host cell is derived from an established expression cell line. The host cell in particular is a eukaryotic cell, such as a mammalian cell, in particular a human cell, or a cell derived therefrom. In particular, the host cell is a blood cell, such as a white blood cell, blood precursor cell or leukemia cell, or a cell derived therefrom. In certain embodiments, the host cell is a cell of leukocyte origin.

In specific embodiments, the host cell is derived from human myeloid leukaemia cells. Specific examples of host cells are K562, NM-F9, NM-D4, NM-H9D8, NM-H9D8-E6, NM-H9D8-E6Q12, GT-2X, GT-5s and cells derived from anyone of said host cells. K562 is a human myeloid leukemia cell line present in the American Type Culture Collection (ATCC CCL-243). The remaining cell lines are derived from K562 cells and have been selected for specific glycosylation features. Cell lines derived from K562 can be cultivated and maintained under the well-known conditions suitable for K562. All these cell lines except for K562 cells were deposited according to the Budapest treaty. Information on the deposition can be found at the end of the specification.

Exemplary host cells are also described, for example, in WO 2008/028686. In certain embodiments, the host cell is optimized for expression of glycoproteins having a specific glycosylation pattern. In particular, the codon usage in the coding region and/or the promoter and the further elements of the expression cassette or vector are compatible with and in particular optimized for the type of host cell used.

In certain embodiments, the host cell is an isolated host cell. In specific embodiments, the host cell is not present in the human or animal body.

The host cell may be transiently or stably transfected with the expression cassette or vector according to the invention. Stable transfection is preferred, in particular by integration of the expression cassette into the genome of the host cell. Transfection methods for stable or transient transfection are commonly known in the art. In certain embodiments, the host cell is transfected with the vector which comprises the expression cassette with the coding region comprising a nucleic acid sequence coding for a polypeptide of interest.

The Production Method

According to a further aspect, the present invention provides a method for recombinantly producing a polypeptide of interest, comprising the steps of
(a) providing a host cell which comprises an expression cassette comprising, functionally linked to each other,
    (i) a locus control region comprising at least a functional part of the locus control region of the human β-globin gene cluster or the human α-globin gene cluster;
    (ii) a promoter region comprising at least a functional part of the promoter of the human $^A\gamma$ globin gene; and
    (iii) a coding region comprising a nucleic acid sequence encoding the polypeptide of interest;
(b) culturing the host cell under conditions at which the host cell expresses the polypeptide of interest; and
(c) isolating the polypeptide of interest.

The host cell in particular comprises an expression cassette as defined herein, having one or more of the elements defined herein.

Suitable conditions for culturing the host cells and expressing the polypeptide of interest depend on the specific host cell, vector and expression cassette used in the method. The skilled person can readily determine suitable conditions and they are also already known in the art for a plurality of host cells. In certain embodiments, the host cell is transfected with a vector comprising the expression cassette and further comprising a selectable marker gene. In these embodiments, the culturing conditions in step (b) may include the presence of a corresponding selection agent in the cell culture medium.

Isolation of the polypeptide of interest in particular refers to the separation of the polypeptide of interest from the remaining components of the cell culture. In certain embodiments, the coding region of the expression cassette further comprises a nucleic acid sequence coding for a signal peptide for secretory expression, and in step (b) the polypeptide of interest is secreted by the host cell. In these embodiments, step (c) in particular comprises separating the cell culture medium comprising the polypeptide of interest from the host cells, for example by centrifugation, and separating the polypeptide of interest from some or most of the components of the cell culture medium, for example by chromatographic methods. Suitable methods and means for isolating the polypeptide of interest are known in the art and can be readily applied by the skilled person.

In certain embodiments, the method for producing a polypeptide of interest further comprises after step (c) the step of
(d) formulating the polypeptide of interest as a pharmaceutical composition.

Formulating the polypeptide of interest as a pharmaceutical composition in particular comprises exchanging the buffer solution or buffer solution components of the composition comprising the polypeptide of interest. Furthermore, the formulation step may include lyophilization of the polypeptide of interest. In particular, the polypeptide of interest is transferred into a composition only comprising pharmaceutically acceptable ingredients.

Numeric ranges described herein are inclusive of the numbers defining the range. The headings provided herein are not limitations of the various aspects or embodiments of this invention which can be read by reference to the specification as a whole. According to one embodiment, subject matter described herein as comprising certain steps in the case of methods or as comprising certain ingredients in the case of compositions refers to subject matter consisting of the respective steps or ingredients. It is preferred to select and combine specific aspects and embodiments described herein and the specific subject-matter arising from a respective combination of specific embodiments also belongs to the present disclosure.

FIGURES

FIG. 1 shows the structure of the human globin gene clusters including the locus control region (LCR) with the different DNase hypersensitivity sites (HS) and the different globin genes. A: human β-globin gene cluster on chromosome 11; B: human α-globin gene cluster on chromosome 16.

FIG. 2 shows the elements of exemplary expression cassettes as used in the vectors pHBG1A-E. HS: DNase hypersensitivity site; $^A\gamma$-Prom: promoter of the $^A\gamma$ globin gene; CS: coding sequence/cloning site; γpA: polyadenylation signal of the $^A\gamma$ globin gene; $^A\gamma$-ENh: 3' enhancer of the $^A\gamma$ globin gene.

Figure 3:
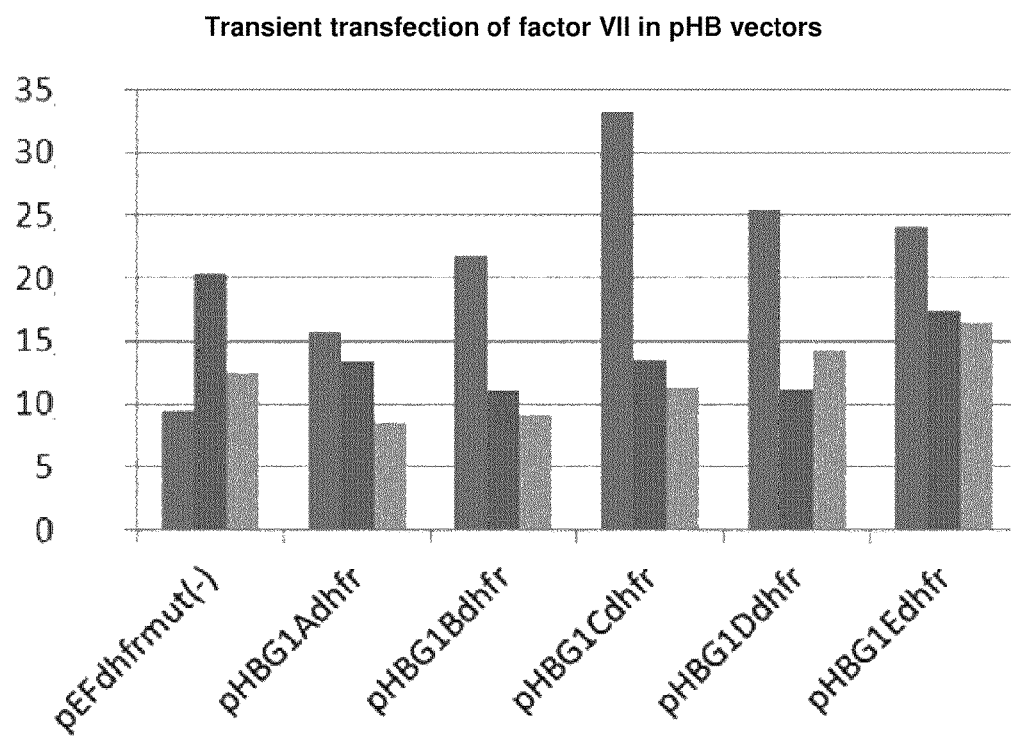

FIG. 3 shows the factor VII protein yield obtained after transient transfection of different vectors comprising the coding sequence of factor VII. Vectors comprising the expression cassettes shown in FIG. 2 with the coding sequence of factor VII introduced into the cloning site and a gene encoding DHFR as amplifiable selectable marker were transiently transfected into NM-H9D8 cells. Total yield of factor VII was determined after cultivation. pEFdhfrmut (−): control vector with factor VII coding sequence. The results of three independent experiments are shown.

Figure 4:
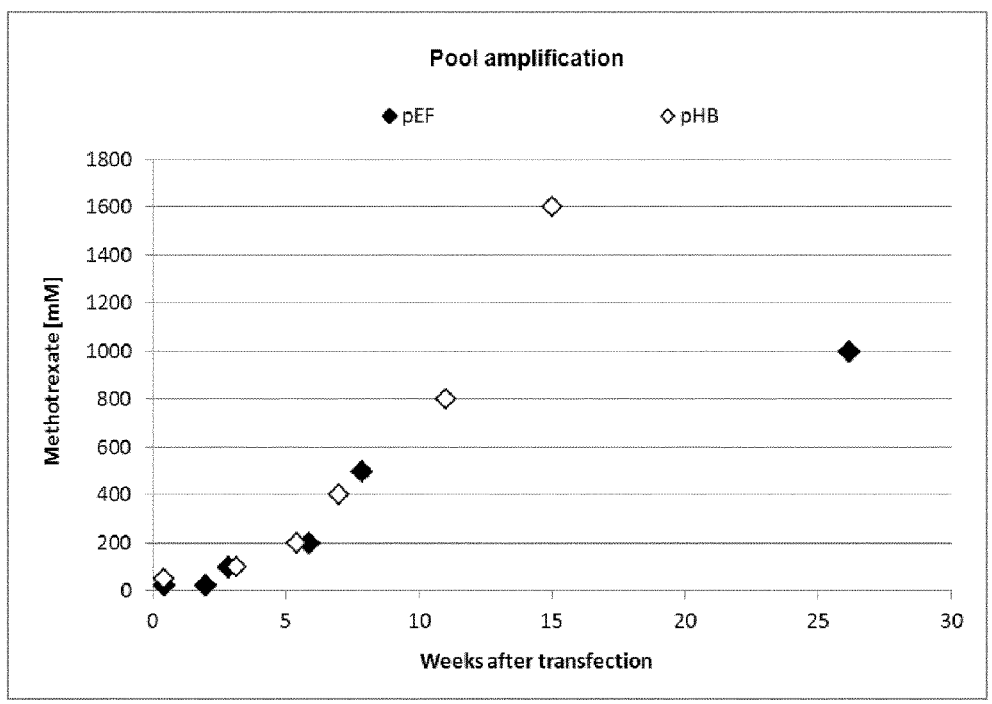

FIG. 4 shows a comparison of stable transfection of a vector according to the invention and a control vector encoding an antibody. NM-H9D8-E6Q12 cells were stably transfected with the control vector pEF or the vector pHB according to the invention. Both vectors comprise a coding sequence for an antibody and a gene encoding DHFR as amplifiable selectable marker. For amplification of the vector in the cells, the selection pressure, i.e. the concentration of the selection agent methotrexate in the culture medium, was stepwise increased. The graph shows the maximum selection pressure which was possible for the respective vector after a given cultivation time. A higher possible selection pressure (methotrexate concentration) indicates a stronger amplification of the vector in the transfected cells, which should result in a higher production of the protein of interest.

Figure 5:
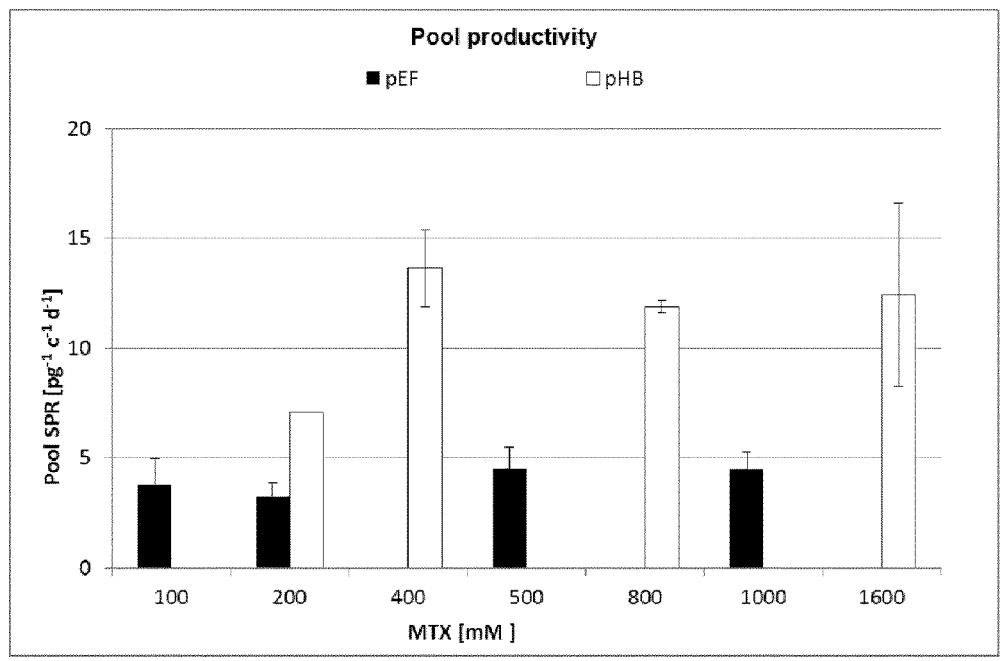

FIG. 5 shows the pool productivity of the stably transfected cells of FIG. 4. The antibody production in picogram per cell per day is shown for the different selection pressures for the vector according to the invention and the control vector.

Figure 6:
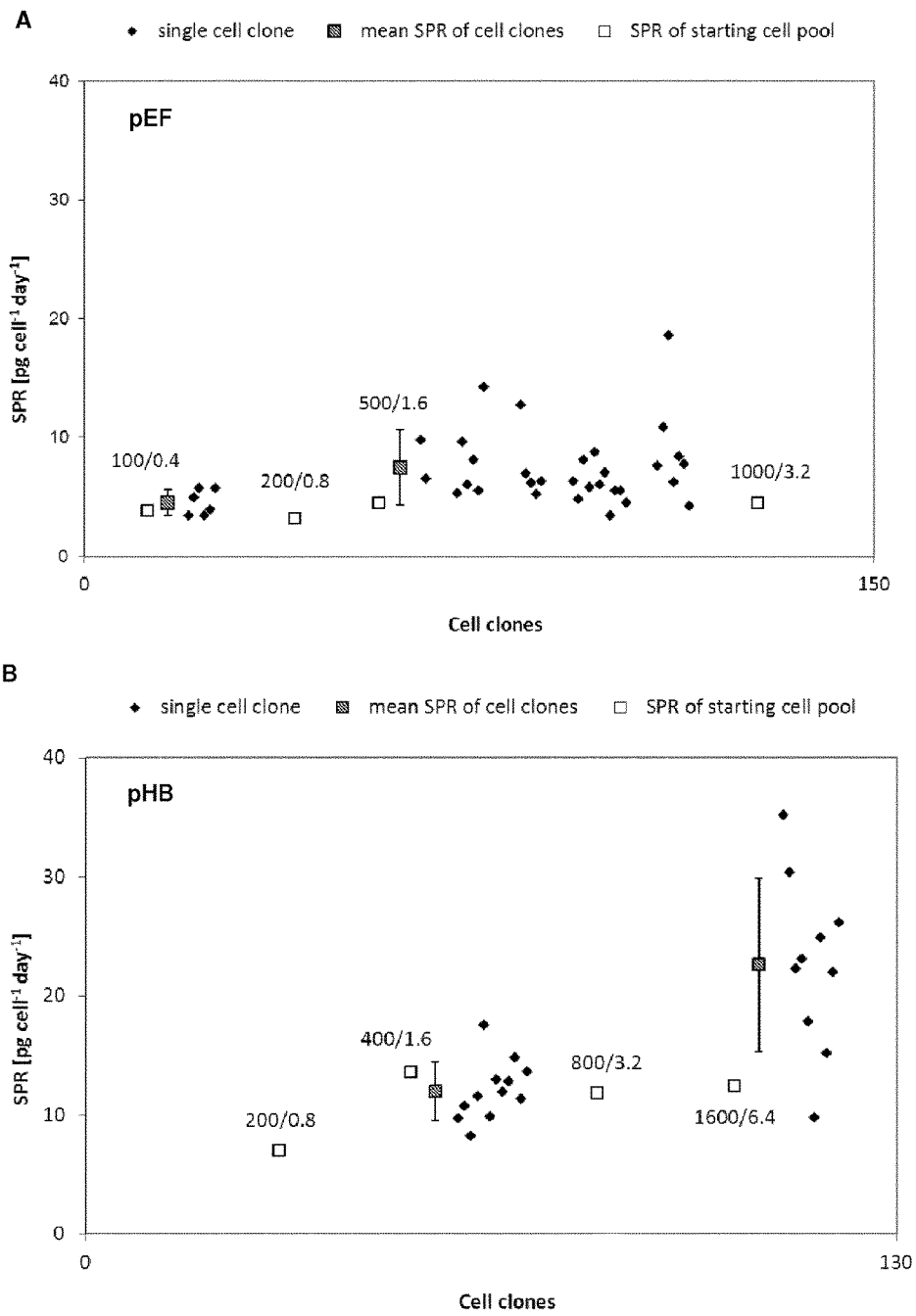

FIG. 6 shows the increase in productivity of the stably transfected cells of FIG. 4 by amplification of the vector due to the selection pressure. The antibody production in picogram per cell per day is shown for the different selection pressures for the starting cell pool, for the cell pool after amplification and for single cell clones after amplification. A: control vector pEF; B: vector pHB according to the invention.

EXAMPLES

Example 1: Construction of Vectors Comprising the Human $^A\gamma$ Globin Promoter and Elements of the Locus Control Regions of the Human Globin Gene Clusters For construction of the globin vectors, the enhancer and promoter regions of a parent vector (e.g. pEF having a puromycin or neomycin resistance gene or a dhfr gene as selectable marker) were removed. The human $^A\gamma$ globin promoter, polyadenylation signal and 3' enhancer regions and different constructs of the locus control regions of the human globin gene clusters were synthesized and cloned into the vector at the appropriate sites. FIG. 2 shows exemplary constructs of the expression cassettes of the constructed vectors. Then a nucleic acid sequence coding for a polypeptide of interest was introduced into the cloning site.

Example 2: Transient Transfection of the Globin Vectors

Transient transfection was performed with Lipofectamine® LTX and Plus™ Reagent according to the manufacturer's instructions. Briefly, 2×10$^5$ cells were seeded in 6-well plates during their logarithmic growth phase. Plasmid DNA was diluted in Opti-MEM I Reduced Serum Medium and PlusTm-Reagent. After an incubation time (15 min), Lipofectamine® LTX was added to the solution. After further incubation (30 min), the mixture was dripped in the cell suspension. Expression was analyzed after 72 hours by ELISA. Higher protein titers were achieved by the vectors pHBG1Cdhfr, pHBG1Ddhfr and pHBG1Edhfr in comparison to the vector pEFdhfrmut(−) (FIG. 3).

Example 3: Stable Transfection of the Globin Vectors

Transfection of the cell line NM-H9D8 was performed by nucleofection (Nucleofector™ Technology, Amaxa) using plasmid DNA of the two expression plasmids coding for the antibody heavy and light chain, respectively (both linearized) according to the manufacturer's instructions. For selection and amplification of antibody producing pools, methotrexate and puromycin were added at increasing concentrations and pools were screened for secretion of active antibody molecules.

Pools transfected with pHB plasmids could be amplified in a shorter time period (FIG. 4) and led to higher protein levels (FIG. 5) which could be confirmed for resulting single cell clones, respectively (FIG. 6).

Identification of the Deposited Biological Material

The cell lines DSM ACC 2606 and DSM ACC 2605 were deposited at the DSMZ—Deutsche Sammlung von Mikroorganismen und Zellkulturen GmbH, Mascheroder Weg 1b, 38124 Braunschweig (DE) by Nemod Biotherapeutics GmbH & Co. KG, Robert-Rössle-Str. 10, 13125 Berlin (DE) on Aug. 14, 2003. Glycotope is entitled to refer to these biological materials since they were in the meantime assigned from Nemod Biotherapeutics GmbH & Co. KG to Glycotope GmbH.

The cell lines DSM ACC 2806, DSM ACC 2807, DSM ACC 2856, DSM ACC 2858 and DSM ACC 3078 were deposited at the DSMZ—Deutsche Sammlung von Mikroorganismen und Zellkulturen GmbH, Inhoffenstraße 7B, 38124 Braunschweig (DE) by Glycotope GmbH, Robert-Rössle-Str. 10, 13125 Berlin (DE) on the dates indicated in the following table.

| Name of the Cell Line | Accession Number | Depositor | Date of Deposition |
|---|---|---|---|
| NM-F9 | DSM ACC 2606 | Nemod Biotherapeutics | Aug. 14, 2003 |
| NM-D4 | DSM ACC 2605 | Nemod Biotherapeutics | Aug. 14, 2003 |
| NM-H9D8 | DSM ACC 2806 | Glycotope GmbH | Sep. 15, 2006 |
| NM-H9D8-E6 | DSM ACC 2807 | Glycotope GmbH | Oct. 5, 2006 |
| NM-H9D8-E6Q12 | DSM ACC 2856 | Glycotope GmbH | Aug. 8, 2007 |
| GT-2x | DSM ACC 2858 | Glycotope GmbH | Sep. 7, 2007 |
| GT-5s | DSM ACC 3078 | Glycotope GmbH | Jul. 28, 2010 |

The invention claimed is:

1. A method for recombinantly producing a polypeptide of interest, comprising the steps of
  (a) providing a host cell which comprises an expression cassette comprising, functionally linked to each other,
    (i) a locus control region comprising at least a functional part of the locus control region of the human β-globin gene cluster or the human α-globin gene cluster;
    (ii) a promoter region comprising at least a functional part of the promoter of the human $^A\gamma$ globin gene or a homologue thereof; and
    (iii) a coding region comprising a nucleic acid sequence encoding the polypeptide of interest and a nucleic acid sequence coding for a signal peptide for secretory expression;
  (b) culturing the host cell under conditions at which the host cell expresses and secretes the polypeptide of interest; and
  (c) isolating the polypeptide of interest.

2. The method according to claim 1, further comprising after step (c) the step of (d) formulating the polypeptide of interest as a pharmaceutical composition.

3. The method according to claim 1, wherein the locus control region of the expression cassette comprises the core element of the DNAse I hypersensitivity site 2 (HS2) of the human β-globin gene cluster.

4. The method according to claim 3, wherein the locus control region of the expression cassette comprises the M1-core-M2 element of the DNAse I hypersensitivity site 2 (HS2) of the human β-globin gene cluster.

5. The method according to claim 4, wherein the locus control region of the expression cassette comprises at least a part of the hypersensitivity site 2 (HS2) of the human β-globin gene cluster which comprises the nucleic acid sequence of position 741 to 1109 of SEQ ID NO: 1.

6. The method according to claim 3, wherein the locus control region of the expression cassette further comprises the hypersensitivity site 3 (HS3) or a part thereof of the human β-globin gene cluster, and/or the hypersensitivity site 4 (HS4) or a part thereof of the human β-globin gene cluster.

7. The method according to claim 1, wherein the locus control region of the expression cassette comprises the hypersensitivity site 40 (HS40) or a part thereof of the human α-globin gene cluster.

8. The method according to claim 1, wherein the promoter region of the expression cassette comprises nucleotides −384 to +36, with respect to the transcription initiation site, of the human $^A\gamma$ globin gene.

9. The method according to claim 1, wherein the expression cassette further comprises an enhancer region comprising at least a functional part of the 3' enhancer of the human $^A\gamma$ globin gene, functionally linked to the other elements of the expression cassette.

10. The method according to claim 1, wherein the polypeptide of interest is a glycoprotein or a part thereof.

11. The method according to claim 1, wherein the host cell is a white blood cell, blood precursor cell or leukemia cell, or a cell derived therefrom.

12. An expression cassette comprising, functionally linked to each other,
(i) a locus control region comprising at least a functional part of the locus control region of the human β-globin gene cluster or the human α-globin gene cluster;
(ii) a promoter region comprising at least a functional part of the promoter of the human $^A\gamma$ globin gene;
(iii) a coding region comprising a nucleic acid sequence coding for a signal peptide for secretory expression;
(iv) a transcription terminator region; and
(v) an enhancer region comprising at least a functional part of the 3' enhancer of the human $^A\gamma$ globin gene;
wherein the expression cassette does not comprise a nucleic acid sequence coding for the entire human $^A\gamma$ globin.

13. The expression cassette according to claim 12, wherein the locus control region comprises the core element of the DNAse I hypersensitivity site 2 (HS2) of the human β-globin gene cluster.

14. The expression cassette according to claim 13, wherein the locus control region comprises the M1-core-M2 element of the DNAse I hypersensitivity site 2 (HS2) of the human β-globin gene cluster.

15. The expression cassette according to claim 14, wherein the locus control region comprises at least a part of the hypersensitivity site 2 (HS2) of the human β-globin gene cluster which comprises the nucleic acid sequence of position 741 to 1109 of SEQ ID NO: 1.

16. The expression cassette according to claim 13, wherein the locus control region further comprises the hypersensitivity site 3 (HS3) or a part thereof of the human β-globin gene cluster, and/or the hypersensitivity site 4 (HS4) or a part thereof of the human β-globin gene cluster.

17. The expression cassette according to claim 12, wherein the locus control region comprises the hypersensitivity site 40 (HS40) or a part thereof of the human α-globin gene cluster.

18. The expression cassette according to claim 12, wherein the promoter region comprises nucleotides −384 to +36, with respect to the transcription initiation site, of the human $^A\gamma$ globin gene.

19. The expression cassette according to claim 12, wherein the enhancer region comprises the nucleic acid sequence of position 2136 to 2881 of SEQ ID NO: 1.

20. The expression cassette according to claim 12, further comprising a cloning site which comprises at least one recognition sequence of a restriction enzyme.

21. The expression cassette according to claim 12, wherein the coding region comprises a nucleic acid sequence coding for a polypeptide of interest.

22. A host cell comprising the expression cassette according to claim 12.

23. The host cell according to claim 22, being a white blood cell, blood precursor cell or leukemia cell, or a cell derived therefrom.

* * * * *

SEQUENCE LISTING

```
<160> NUMBER OF SEQ ID NOS: 5

<210> SEQ ID NO 1
<211> LENGTH: 2899
<212> TYPE: DNA
<213> ORGANISM: artificial sequences
<220> FEATURE:
<221> NAME/KEY: source
<222> LOCATION: 1..2899
<223> OTHER INFORMATION: /mol_type="DNA"
      /note="expression cassette HBG1A"
      /organism="artificial sequences"

<400> SEQUENCE: 1
tcgcgatgat caacttttag agagctcttg gggaccccag tacacaagag gggacgcagg      60
gtatatgtag acatctcatt ctttttctta gtgtgagaat aagaatagcc atgacctgag     120
```

```
tttatagaca atgagcccctt ttctctctcc cactcagcag ctatgagatg gcttgccctg    180
cctctctact aggctgactc actccaaggc ccagcaatgg gcagggctct gtcagggctt    240
tgatagcact atctgcagag ccagggccga aaggggtgg actccagaga ctctcctgat    300
cattaattaa gctactgctc atgggccctg tgctgcactg atgaggagga tcagatggat    360
ggggcaatga agcaaaggaa tcattctgtg gataaaggag acagccatga agaagtctat    420
gactgtaaat ttgggagcag gagtctctaa ggacttggat ttcaaggaat tttgactcag    480
caaacacaag accctcacgg tgactttgcg agctggtgtg ccagatgtgt ctatcagagg    540
ttccagggag ggtggggtgg ggtcagggct ggccaccagc tatcagggcc cagatgggtt    600
ataggctggc aggctcagat aggtggttag gtcaggttgg tggtgctggg tggagtccat    660
gactcccagg agccaggaga gatagaccat gagtagaggg cagacatggg aaaggtgggg    720
gaggcacagc atagcttaat taagccagtt tttccttagt tcctgttaca tttctgtgtg    780
tctccattag tgacctccca tagtccaagc atgagcagtt ctggccaggc ccctgtcggg    840
gtcagtgccc cacccccgcc ttctggttct gtgtaacctt ctaagcaaac cttctggctc    900
aagcacagca atgctgagtc atgatgagtc atgctgaggc ttagggtgtg tgcccagatg    960
ttctcagcct agagtgatga ctcctatctg ggtccccagc aggatgctta cagggcagat   1020
ggcaaaaaaa aggagaagct gaccacctga ctaaaactcc acctcaaacg gcatcataaa   1080
gaaaatggat gcctgagaca gaatgtgacg catttaaatg atcctcactg gagctacaga   1140
caagaaggta aaaaacggct gacaaaagaa gtcctggtat cctctatgat gggagaagga   1200
aactagctaa agggaagaat aaattagaga aaaactggaa tgactgaatc ggaacaaggc   1260
aaaggctata aaaaaaatta agcagcagta tcctcttggg ggccccttcc ccacactatc   1320
tcaatgcaaa tatctgtctg aaacggtccc tggctaaact ccacccatgg gttggccagc   1380
cttgccttga ccaatagcct tgacaaggca aacttgacca atagtcttag agtatccagt   1440
gaggccaggg gccggcggct ggctagggat gaagaataaa aggaagcacc cttcagcagt   1500
tccacacact cgcttctgga acgtctgaga ttatcaataa gctcctagtc cagacgccaa   1560
gcttggtacc gagctcggat ccactagtaa cggccggcca gtgtgctgga attctgcaga   1620
tatccatcac actgcccggg cggccgctcg agcatcgatc tagagcctct tgcccatgat   1680
tcagagcttt caaggatagg ctttattctg caagcaatac aaataataaa tctattctgc   1740
tgagagatca cacatgattt tcttcagctc tttttttttac atcttttttaa atatatgagc   1800 cacaaagggt ttatattgag ggaagtgtgt atgtgtattt ctgcatgcct gtttgtgttt   1860
gtggtgtgtg catgctcctc atttattttt atatgagatg tgcattttga tgagcaaata   1920
aaagcagtaa agacacttgt acacgggagt tctgcaagtg ggagtaaatg gtgttggaga   1980
aatccggtgg gaagaaagac ctctatagga caggacttct cagaaacaga tgttttggaa   2040
gagatgggaa aaggttcagt gaagacctgg gggctggatt gattgcagct gagtagcaag   2100
gatggttctt aatgaaggga aagtgttcca agctggaatt caaggtttag tcaggtgtag   2160
caattctatt ttattaggag gaatactatt tctaatggca cttagctttt cacagcccctt   2220 gtggatgcct aagaaagtga aattaatccc atgccctcaa gtgtgcagat tggtcacagc   2280
atttcaaggg agagacctca ttgtaagact ctggggagg tggggactta ggtgtaagaa   2340
atgaatcagc agaggctcac aagtcagcat gagcatgtta tgtctgagaa acagaccagc   2400
actgtgagat caaaatgtag tgggaagaat ttgtacaaca ttaattggaa ggtttactta   2460
atggaatttt tgtatagttg gatgttagtg catctctata agtaagagtt taatatgatg   2520
```

```
gtgttacgga cctggtgttt gtgtctcctc aaaattcaca tgctgaatcc ccaactccca    2580
actgacctta tctgtggggg aggcttttga aaagtaatta ggtttagctg agctcataag    2640
agcagatccc catcataaaa ttattttcct tatcagaagc agagagacaa gccatttctc    2700
tttcctcccg gtgaggacac agtgagaagt ccgccatctg caatccagga agagaaccct    2760
gaccacgagt cagccttcag aaatgtgaga aaaaactctg ttgttgaagc cacccagtct    2820
tttgtatttt gttatagcac cttacactga gtaaggcaga tgaagaagga gaaaaaaata    2880
acagctggtt aactacgta                                                 2899
```

<210> SEQ ID NO 2
<211> LENGTH: 2609
<212> TYPE: DNA
<213> ORGANISM: artificial sequences
<220> FEATURE:
<221> NAME/KEY: source
<222> LOCATION: 1..2609
<223> OTHER INFORMATION: /mol_type="DNA"
    /note="expression cassette HBG1B"
    /organism="artificial sequences"

<400> SEQUENCE: 2

```
tcgcgatgat cattaattaa gctactgctc atgggccctg tgctgcactg atgaggagga      60
tcagatggat ggggcaatga agcaaaggaa tcattctgtg gataaaggag acagccatga     120
agaagtctat gactgtaaat ttgggagcag gagtctctaa ggacttggat ttcaaggaat     180
tttgactcag caaacacaag accctcacgg tgactttgcg agctggtgtg ccagatgtgt     240
ctatcagagg ttccagggag ggtggggtgg ggtcagggct ggccaccagc tatcagggcc     300
cagatgggtt ataggctggc aggctcagat aggtggttag gtcaggttgg tggtgctggg     360
tggagtccat gactcccagg agccaggaga gatagaccat gagtagaggg cagacatggg     420
aaaggtgggg gaggcacagc atagcttaat taagccagtt tttccttagt tcctgttaca     480
tttctgtgtg tctccattag tgacctccca tagtccaagc atgagcagtt ctggccaggc     540
ccctgtcggg gtcagtgccc cacccccgcc ttctggttct gtgtaacctt ctaagcaaac     600
cttctggctc aagcacagca atgctgagtc atgatgagtc atgctgaggc ttagggtgtg     660
tgcccagatg ttctcagcct agagtgatga ctcctatctg ggtccccagc aggatgctta     720
cagggcagat ggcaaaaaaa aggagaagct gaccacctga ctaaaactcc acctcaaacg     780
gcatcataaa gaaaatggat gcctgagaca gaatgtgacg catttaaatg atcctcactg     840
gagctacaga caagaaggta aaaaacggct gacaaaagaa gtcctggtat cctctatgat     900
gggagaagga aactagctaa agggaagaat aaattagaga aaaactggaa tgactgaatc     960
ggaacaaggc aaaggctata aaaaaaatta agcagcagta tcctcttggg ggcccttcc     1020 ccacactatc tcaatgcaaa tatctgtctg aaacggtccc tggctaaact ccacccatgg    1080
gttggccagc cttgccttga ccaatagcct tgacaaggca aacttgacca atagtcttag    1140
agtatccagt gaggccaggg gccggcggct ggctagggat gaagaataaa aggaagcacc    1200
cttcagcagt tccacacact cgcttctgga acgtctgaga ttatcaataa gctcctagtc    1260
cagacgccaa gcttggtacc gagctcggat ccactagtaa cggccggcca gtgtgctgga    1320
attctgcaga tatccatcac actgcccggg cggccgctcg agcatcgatc tagagcctct    1380
tgcccatgat tcagagcttt caaggatagg ctttattctg caagcaatac aaataataaa    1440
tctattctgc tgagagatca cacatgattt tcttcagctc ttttttttac atctttttaa    1500
atatatgagc cacaaagggt ttatattgag ggaagtgtgt atgtgtattt ctgcatgcct    1560
```

| | |
|---|---|
| gtttgtgttt gtggtgtgtg catgctcctc atttattttt atatgagatg tgcattttga | 1620 |
| tgagcaaata aaagcagtaa agacacttgt acacggagt tctgcaagtg ggagtaaatg | 1680 |
| gtgttggaga atccggtgg gaagaaagac ctctatagga caggacttct cagaaacaga | 1740 |
| tgttttggaa gagatgggaa aaggttcagt gaagacctgg gggctggatt gattgcagct | 1800 |
| gagtagcaag gatggttctt aatgaaggga aagtgttcca agctggaatt caaggtttag | 1860 |
| tcaggtgtag caattctatt ttattaggag gaatactatt tctaatggca cttagctttt | 1920 |
| cacagccctt gtggatgcct aagaaagtga aattaatccc atgccctcaa gtgtgcagat | 1980 |
| tggtcacagc atttcaaggg agagacctca ttgtaagact ctgggggagg tggggactta | 2040 |
| ggtgtaagaa atgaatcagc agaggctcac aagtcagcat gagcatgtta tgtctgagaa | 2100 |
| acagaccagc actgtgagat caaaatgtag tgggaagaat ttgtacaaca ttaattggaa | 2160 |
| ggtttactta atggaatttt tgtatagttg gatgttagtg catctctata agtaagagtt | 2220 |
| taatatgatg gtgttacgga cctggtgttt gtgtctcctc aaaattcaca tgctgaatcc | 2280 |
| ccaactccca actgacctta tctgtggggg aggcttttga aaagtaatta ggtttagctg | 2340 |
| agctcataag agcagatccc catcataaaa ttattttcct tatcagaagc agagagacaa | 2400 |
| gccatttctc tttcctcccg gtgaggacac agtgagaagt ccgccatctg caatccagga | 2460 |
| agagaaccct gaccacgagt cagccttcag aaatgtgaga aaaaactctg ttgttgaagc | 2520 |
| cacccagtct tttgtatttt gttatagcac cttacactga gtaaggcaga tgaagaagga | 2580 |
| gaaaaaaata acagctggtt aactacgta | 2609 |

<210> SEQ ID NO 3
<211> LENGTH: 2176
<212> TYPE: DNA
<213> ORGANISM: artificial sequences
<220> FEATURE:
<221> NAME/KEY: source
<222> LOCATION: 1..2176
<223> OTHER INFORMATION: /mol_type="DNA"
      /note="expression cassette HBG1C"
      /organism="artificial sequences"

<400> SEQUENCE: 3

| | |
|---|---|
| tcgcgatgat cattaattaa gccagttttt ccttagttcc tgttacattt ctgtgtgtct | 60 |
| ccattagtga cctcccatag tccaagcatg agcagttctg gccaggcccc tgtcggggtc | 120 |
| agtgccccac cccgccttc tggttctgtg taaccttcta agcaaacctt ctggctcaag | 180 |
| cacagcaatg ctgagtcatg atgagtcatg ctgaggctta gggtgtgtgc ccagatgttc | 240 |
| tcagcctaga gtgatgactc ctatctgggt ccccagcagg atgcttacag ggcagatggc | 300 |
| aaaaaaaagg agaagctgac cacctgacta aaactccacc tcaaacggca tcataaagaa | 360 |
| aatggatgcc tgagacagaa tgtgacgcat ttaaatgatc ctcactggag ctacagacaa | 420 |
| gaaggtaaaa aacggctgac aaaagaagtc ctggtatcct ctatgatggg agaaggaaac | 480 |
| tagctaaagg gaagaataaa ttagagaaaa actggaatga ctgaatcgga acaaggcaaa | 540 |
| ggctataaaa aaaattaagc agcagtatcc tcttgggggc cccttcccca cactatctca | 600 |
| atgcaaatat ctgtctgaaa cggtcccctgg ctaaactcca cccatgggtt ggccagcctt | 660 |
| gccttgacca atagccttga caaggcaaac ttgaccaata gtcttagagt atccagtgag | 720 |
| gccaggggcc ggcggctggc tagggatgaa gaataaaagg aagcacccttt cagcagttcc | 780 |
| acacactcgc ttctgaaacg tctgagatta tcaataagct cctagtccag acgccaagct | 840 |
| tggtaccgag ctcggatcca ctagtaacgg ccggccagtg tgctggaatt ctgcagatat | 900 |

```
ccatcacact gcccgggcgg ccgctcgagc atcgatctag agcctcttgc ccatgattca    960
gagctttcaa ggataggctt tattctgcaa gcaatacaaa taataaatct attctgctga   1020
gagatcacac atgattttct tcagctcttt tttttacatc tttttaaata tatgagccac   1080
aaagggttta tattgaggga agtgtgtatg tgtatttctg catgcctgtt tgtgtttgtg   1140
gtgtgtgcat gctcctcatt tatttttata tgagatgtgc attttgatga gcaaataaaa   1200
gcagtaaaga cacttgtaca cgggagttct gcaagtggga gtaaatggtg ttggagaaat   1260
ccggtgggaa gaaagacctc tataggacag gacttctcag aaacagatgt tttggaagag   1320
atgggaaaag gttcagtgaa gacctggggg ctggattgat gcagctgag  tagcaaggat   1380 ggttcttaat gaagggaaag tgttccaagc tggaattcaa ggtttagtca ggtgtagcaa   1440
ttctatttta ttaggaggaa tactatttct aatggcactt agcttttcac agcccttgtg   1500
gatgcctaag aaagtgaaat taatcccatg ccctcaagtg tgcagattgg tcacagcatt   1560
tcaaggagga gacctcattg taagactctg ggggaggtgg ggacttaggt gtaagaaatg   1620
aatcagcaga ggctcacaag tcagcatgag catgttatgt ctgagaaaca gaccagcact   1680
gtgagatcaa aatgtagtgg gaagaatttg tacaacatta attggaaggt ttacttaatg   1740 gaattttgt  atagttggat gttagtgcat ctctataagt aagagtttaa tatgatggtg   1800
ttacggacct ggtgtttgtg tctcctcaaa attcacatgc tgaatcccca actcccaact   1860
gaccttatct gtggggagg  cttttgaaaa gtaattaggt ttagctgagc tcataagagc   1920
agatccccat cataaaatta ttttccttat cagaagcaga gagacaagcc atttctcttt   1980
cctcccggtg aggacacagt gagaagtccg ccatctgcaa tccaggaaga gaaccctgac   2040
cacgagtcag ccttcagaaa tgtgagaaaa aactctgttg ttgaagccac ccagtctttt   2100 gtatttgtt  atagcacctt acactgagta aggcagatga agaaggagaa aaaaataaca   2160
gctggttaac tacgta                                                  2176
```

<210> SEQ ID NO 4
<211> LENGTH: 2054
<212> TYPE: DNA
<213> ORGANISM: artificial sequences
<220> FEATURE:
<221> NAME/KEY: source
<222> LOCATION: 1..2054
<223> OTHER INFORMATION: /mol_type="DNA"
      /note="expression cassette HBG1D"
      /organism="artificial sequences"

<400> SEQUENCE: 4

```
tcgcgatgat caaagccagt ttttccttag ttcctgttac atttctgtgt gtctccatta     60
gtgacctccc atagtccaag catgagcagt tctggccagg cccctgtcgg ggtcagtgcc    120 ccaccccgc  cttctggttc tgtgtaacct tctaagcaaa ccttctggct caagcacagc    180
aatgctgagt catgatgagt catgctgagg cttagggtgt gtgcccagat gttctcagcc    240
tagagtgatg actcctatct gggtccattt aaatgatcct cactggagct acagacaaga    300
aggtaaaaaa cggctgacaa agaagtcct  ggtatcctct atgatgggag aaggaaacta    360
gctaaaggga agaataaatt agagaaaaac tggaatgact gaatcggaac aaggcaaagg    420
ctataaaaaa aattaagcag cagtatcctc ttggggggcc cttccccaca ctatctcaat    480
gcaaatatct gtctgaaacg gtccctggct aaactccacc catgggttgg ccagccttgc    540
cttgaccaat agccttgaca aggcaaactt gaccaatagt cttagagtat ccagtgaggc    600
caggggccgg cggctggcta gggatgaaga ataaaaggaa gcacccttca gcagttccac    660
```

```
acactcgctt ctggaacgtc tgagattatc aataagctcc tagtccagac gccaagcttg      720
gtaccgagct cggatccact agtaacggcc ggccagtgtg ctggaattct gcagatatcc      780
atcacactgc ccgggcggcc gctcgagcat cgatctagag cctcttgccc atgattcaga      840
gctttcaagg ataggcttta ttctgcaagc aatacaaata ataaatctat tctgctgaga      900
gatcacacat gattttcttc agctcttttt tttacatctt tttaaatata tgagccacaa      960
agggtttata ttgagggaag tgtgtatgtg tatttctgca tgcctgtttg tgtttgtggt     1020
gtgtgcatgc tcctcattta tttttatatg agatgtgcat tttgatgagc aaataaaagc     1080
agtaaagaca cttgtacacg ggagttctgc aagtgggagt aaatggtgtt ggagaaatcc     1140
ggtgggaaga aagacctcta taggacagga cttctcagaa acagatgttt tggaagagat     1200
gggaaaaggt tcagtgaaga cctgggggct ggattgattg cagctgagta gcaaggatgg     1260
ttcttaatga agggaaagtg ttccaagctg gaattcaagg tttagtcagg tgtagcaatt     1320
ctattttatt aggaggaata ctatttctaa tggcacttag cttttcacag cccttgtgga     1380
tgcctaagaa agtgaaatta atcccatgcc ctcaagtgtg cagattggtc acagcatttc     1440
aagggagaga cctcattgta agactctggg ggaggtgggg acttaggtgt aagaaatgaa     1500
tcagcagagg ctcacaagtc agcatgagca tgttatgtct gagaaacaga ccagcactgt     1560
gagatcaaaa tgtagtggga agaatttgta caacattaat tggaaggttt acttaatgga     1620 attttgtat agttggatgt tagtgcatct ctataagtaa gagtttaata tgatggtgtt     1680
acggacctgg tgtttgtgtc tcctcaaaat tcacatgctg aatccccaac tcccaactga     1740
ccttatctgt gggggaggct tttgaaaagt aattaggttt agctgagctc ataagagcag     1800
atccccatca taaaattatt ttccttatca gaagcagaga acaagccat ttctctttcc      1860 tcccggtgag gacacagtga gaagtccgcc atctgcaatc caggaagaga accctgacca     1920
cgagtcagcc ttcagaaatg tgagaaaaaa ctctgttgtt gaagccaccc agtcttttgt     1980
attttgttat agcaccttac actgagtaag gcagatgaag aaggagaaaa aaataacagc     2040
tggttaacta cgta                                                      2054
```

<210> SEQ ID NO 5
<211> LENGTH: 2160
<212> TYPE: DNA
<213> ORGANISM: artificial sequences
<220> FEATURE:
<221> NAME/KEY: source
<222> LOCATION: 1..2160
<223> OTHER INFORMATION: /mol_type="DNA"
      /note="expression cassette HBG1E"
      /organism="artificial sequences"

<400> SEQUENCE: 5

```
tcgcgatgct ctcaggaaga ccctctggaa cctatcaggg accacagtca gccaggcaag       60
cacatctgcc caagccaagg gtggaggcat gcagctgtgg gggtctgtga aaacacttga      120
gggagcagat aactgggcca accatgactc agtgcttctg gaggccaaca ggactgctga      180
gtcatcctgt gggggtggag gtgggacaag ggaaaggggt gaatggtact gctgattaca      240
acctctggtg ctgcctcccc ctcctgttta tctgagaggg aaggccatgc ccaaagtgtt      300
cacagccagg cttcaggggc aaagcctgac ccagacagta aatacgttct tcatctggag      360
ctgaagaaat tcatttaaat gatcctcact ggagctacag acaagaaggt aaaaaacggc      420
tgacaaaaga agtcctggta tcctctatga tgggagaagg aaactagcta agggaagaa      480 taaattagag aaaaactgga atgactgaat cggaacaagg caaaggctat aaaaaaaatt      540
```

-continued

```
aagcagcagt atcctcttgg gggccccttc cccacactat ctcaatgcaa atatctgtct    600
gaaacggtcc ctggctaaac tccacccatg ggttggccag ccttgccttg accaatagcc    660
ttgacaaggc aaacttgacc aatagtctta gagtatccag tgaggccagg ggccggcggc    720
tggctaggga tgaagaataa aaggaagcac ccttcagcag ttccacacac tcgcttctgg    780
aacgtctgag attatcaata agctcctagt ccagacgcca agcttggtac cgagctcgga    840
tccactagta acggccggcc agtgtgctgg aattctgcag atatccatca cactgcccgg    900
gcggccgctc gagcatcgat ctagagcctc ttgcccatga ttcagagctt tcaaggatag    960
gctttattct gcaagcaata caaataataa atctattctg ctgagagatc acacatgatt   1020
ttcttcagct cttttttta catcttttta aatatatgag ccacaaaggg tttatattga   1080
gggaagtgtg tatgtgtatt tctgcatgcc tgtttgtgtt tgtggtgtgt gcatgctcct   1140
catttatttt tatatgagat gtgcattttg atgagcaaat aaaagcagta aagacacttg   1200
tacacgggag ttctgcaagt gggagtaaat ggtgttggag aaatccggtg ggaagaaaga   1260
cctctatagg acaggacttc tcagaaacag atgttttgga agagatggga aaaggttcag   1320
tgaagacctg ggggctggat tgattgcagc tgagtagcaa ggatggttct taatgaaggg   1380
aaagtgttcc aagctggaat tcaaggttta gtcaggtgta gcaattctat tttattagga   1440
ggaatactat ttctaatggc acttagcttt tcacagccct tgtggatgcc taagaaagtg   1500
aaattaatcc catgccctca agtgtgcaga ttggtcacag catttcaagg gagagacctc   1560
attgtaagac tctgggggag gtggggactt aggtgtaaga aatgaatcag cagaggctca   1620
caagtcagca tgagcatgtt atgtctgaga aacagaccag cactgtgaga tcaaaatgta   1680
gtgggaagaa tttgtacaac attaattgga aggtttactt aatggaattt ttgtatagtt   1740
ggatgttagt gcatctctat aagtaagagt ttaatatgat ggtgttacgg acctggtgtt   1800
tgtgtctcct caaaattcac atgctgaatc cccaactccc aactgacctt atctgtgggg   1860
gaggcttttg aaaagtaatt aggtttagct gagctcataa gagcagatcc ccatcataaa   1920
attattttcc ttatcagaag cagagagaca agccatttct ctttcctccc ggtgaggaca   1980
cagtgagaag tccgccatct gcaatccagg aagagaaccc tgaccacgag tcagccttca   2040
gaaatgtgag aaaaaactct gttgttgaag ccacccagtc ttttgtattt tgttatagca   2100
ccttacactg agtaaggcag atgaagaagg agaaaaaaat aacagctggt taactacgta   2160
```